(12) United States Patent
Lyu et al.

(10) Patent No.: US 7,129,202 B2
(45) Date of Patent: Oct. 31, 2006

(54) GEMINI SURFACTANTS AND METHODS FOR PREPARING MESOPOROUS MATERIALS USING THE SAME

(75) Inventors: Yi Yeol Lyu, Daejeon-Shi (KR); Seok Chang, Daejeon-Shi (KR); Ji Man Kim, Gyeonggi-Do (KR); Jae Geun Park, Daejeon-Shi (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 285 days.

(21) Appl. No.: 10/649,823

(22) Filed: Aug. 28, 2003

(65) Prior Publication Data

US 2004/0138087 A1 Jul. 15, 2004

(30) Foreign Application Priority Data

Aug. 28, 2002 (KR) .................. 10-2002-0051065
Nov. 18, 2002 (KR) .................. 10-2002-0071571

(51) Int. Cl.
*C11D 1/62* (2006.01)
*C11D 9/36* (2006.01)
*C01B 33/20* (2006.01)

(52) U.S. Cl. .................. 510/504; 510/466; 423/335
(58) Field of Classification Search .............. 510/504, 510/466; 423/335
See application file for complete search history.

(56) References Cited

U.S. PATENT DOCUMENTS

| | | | |
|---|---|---|---|
| 5,057,296 A | 10/1991 | Beck | |
| 5,102,643 A | 4/1992 | Kresge et al. | |
| 6,027,706 A | 2/2000 | Pinnavaia et al. | |
| 6,054,111 A | 4/2000 | Antonietti et al. | |
| 6,183,550 B1 * | 2/2001 | Conner et al. | ........... 106/209.1 |
| 6,358,914 B1 * | 3/2002 | Gabriel et al. | ............... 510/528 |
| 6,528,034 B1 * | 3/2003 | Pinnavaia et al. | .......... 423/335 |

OTHER PUBLICATIONS

Dongyuan Zhao et al., *Science*, vol. 279, No. 5350, (Jan. 23, 1998), pp. 450-451 and pp. 548-552.
Qisheng Huo et al., *Chem. Mater.* vol. 8, (1996), pp. 1147-1160.
Qisheng Huo et al., *Science*, vol. 268, (Jun. 2, 1995), pp. 1324-1327.

\* cited by examiner

*Primary Examiner*—Charles Boyer
(74) *Attorney, Agent, or Firm*—Harness, Dickey & Pierce, P.L.C.

(57) ABSTRACT

Disclosed herein are a novel gemini surfactant and a method for preparing a mesoporous material using the gemini surfactant. The method for preparing a mesoporous material uses the novel gemini surfactant as a structure-directing agent to provide a mesoporous material has a pore size of 10 nm or less with uniform pore size distribution.

11 Claims, 16 Drawing Sheets

GEMINI SURFACTANTS AND METHODS FOR PREPARING MESOPOROUS MATERIALS USING THE SAME

BACKGROUND OF THE INVENTION

This non-provisional application claims priority under 35 U.S.C. § 119(a) on Korean Patent Application Nos. 2002-51065 filed on Aug. 28, 2002 and 02-71571 filed on Nov. 18, 2002, which are herein incorporated by references.

FIELD OF THE INVENTION

The present invention relates to a novel gemini surfactant and a method for preparing a mesoporous material using the gemini surfactant, and more particularly to a novel gemini surfactant containing siloxane moieties in the main chain and a method for preparing a mesoporous material with pore size of 10 nm or less, in which a gemini surfactant is used as a structure-directing agent.

DESCRIPTION OF THE RELATED ART

In 1991, a research team from Mobil produced novel mesoporous molecular sieve materials, denoted as M41S family, using ionic surfactants as structure-directing agents, and presented those in U.S. Pat. Nos. 5,057,296, 5,102,643, etc. Since then, researches on the mesoporous molecular sieve materials have been actively undertaken around the world. Microporous materials such as zeolites and AlPO-type materials have a pore size of 1.5 nm or less, whereas mesoporous materials are increased in their pore size so as to have a pore size of mesoporous range (2~50 nm). Accordingly, the mesoporous materials can be utilized in various applications, e.g., adsorption and separation of molecules larger than a pore size of microporous materials, and catalytic conversion reaction. The M41S family includes MCM-41 materials in which one-dimensional mesoporous pores are arranged in a hexagonal array and MCM-48 materials in which mesoporous pores are connected to each other in a Ia3d cubic structure. U.S. Pat. Nos. 6,027,706 and 6,054,111 and Science, Vol. 279, page 548 (1998) disclose mesoporous materials prepared using nonionic surfactants amphiphilic block copolymers. Science, Vol. 268, page 1324 (1995) and Chemistry of Materials, Vol. 8, page 1147 (1996) suggested that mesoporous materials could be prepared using gemini surfactants. These mesoporous materials having uniform pores possess very large surface areas. Their adsorptive capacity for atoms and molecules is superior. In addition, due to uniform pore size of the mesoporous materials, the mesoporous materials can be applied to molecular sieves and further they are expected to be very useful materials in a variety of industrial applications such as conductive materials, optical display materials, chemical sensors, fine chemistry and bio-catalysis, new insulating materials having different properties, and packaging materials.

One of the most important factors in designing synthesizing the mesoporous materials is a selection of structure-directing agent. Surfactants used as the structure-directing agents for preparing conventional mesoporous materials commonly were in a molecular structure having one hydrophobic moiety and one hydrophilic moiety. Surfactants used in the present invention, however, are gemini surfactants having a hydrophilic moiety indicating two or three ionic portions, and plurality of hydrophobic alkyl chain.

Since the gemini surfactants exhibit excellent interfacial characteristics, such as very low critical micellar concentration, high surface tension depressibility, high foamability and emulsifying capacity, good solubility in water and hard water-resistance, due to their structural characteristics. In view of the molecular structure, the gemini surfactants have been highlighted as a surfactant of new generation. The gemini surfactants have excellent characteristics in formation of micelles, compared to conventional surfactants, due to their intramolecular hydrophobic feature. As mentioned above, the gemini surfactants were first reported in 1995 to be used as structure-directing agents for the preparation of the mesoporous materials. Since then, however, progress of research on the gemini surfactants has been retarded. This is because the preparation of gemini surfactants is difficult compared to that of conventional surfactants while the resulting mesoporous materials have physical properties similar to conventional mesoporous materials. Accordingly, there is a need for designing and preparing gemini surfactants capable of imparting desired physical properties (in particular, hydrophobic surface characteristics and pore size) to mesoporous materials to be prepared.

SUMMARY OF THE INVENTION

It is a feature of the present invention to provide a novel gemini surfactant containing siloxane moieties in the main chain.

It is another feature of the present invention to provide a method for preparing a mesoporous material with pore size of 10 nm or less in which a gemini surfactant is used as a structure-directing agent.

In accordance of a feature of the present invention, there is provided a gemini surfactant represented by the following formula (1):

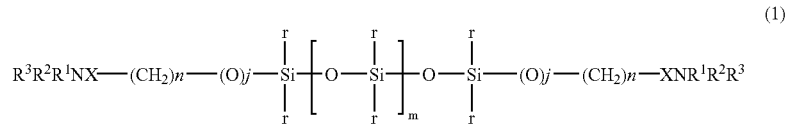

(1)

wherein each of $R^1$ and $R^2$ is independently methyl or ethyl group, $R^3$ is an alkyl group having 5 to 40 carbon atoms, X is a halogen atom, each of r is independently a hydrogen atom, methyl group or an alkoxy group having 1 to 10 carbon atoms, j is 0 or 1, m is an integer of from 0 to 10, and n is an integer of from 1 to 12.

In accordance with another feature of the present invention, there is provided a method of preparing the above gemini surfactant, the method comprising the steps of:

mixing a compound represented by the following formula (2):

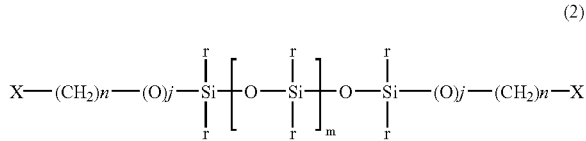

wherein X is a halogen atom, each of r is independently a hydrogen atom, methyl group or an alkyl group having 1 to 10 carbon atoms, j is 0 or 1, m is an integer of from 0 to 10, and n is an integer of from 1 to 12, and a compound represented by the following formula (3):

$$R^3R^2R^1N \quad (3)$$

wherein each of $R^1$ and $R^2$ is independently methyl or ethyl group, and $R^3$ is an alkyl group having 5 to 40 carbon atoms, in a molar ratio of 1:2~1:3; and reacting the mixture in ethanol, acetonitrile, or toluene as a solvent at 30~120° C. for 1~100 hours.

In accordance with yet another feature of the present invention, there is provided a method for preparing a mesoporous material using the above gemini surfactant as a structure-directing agent.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
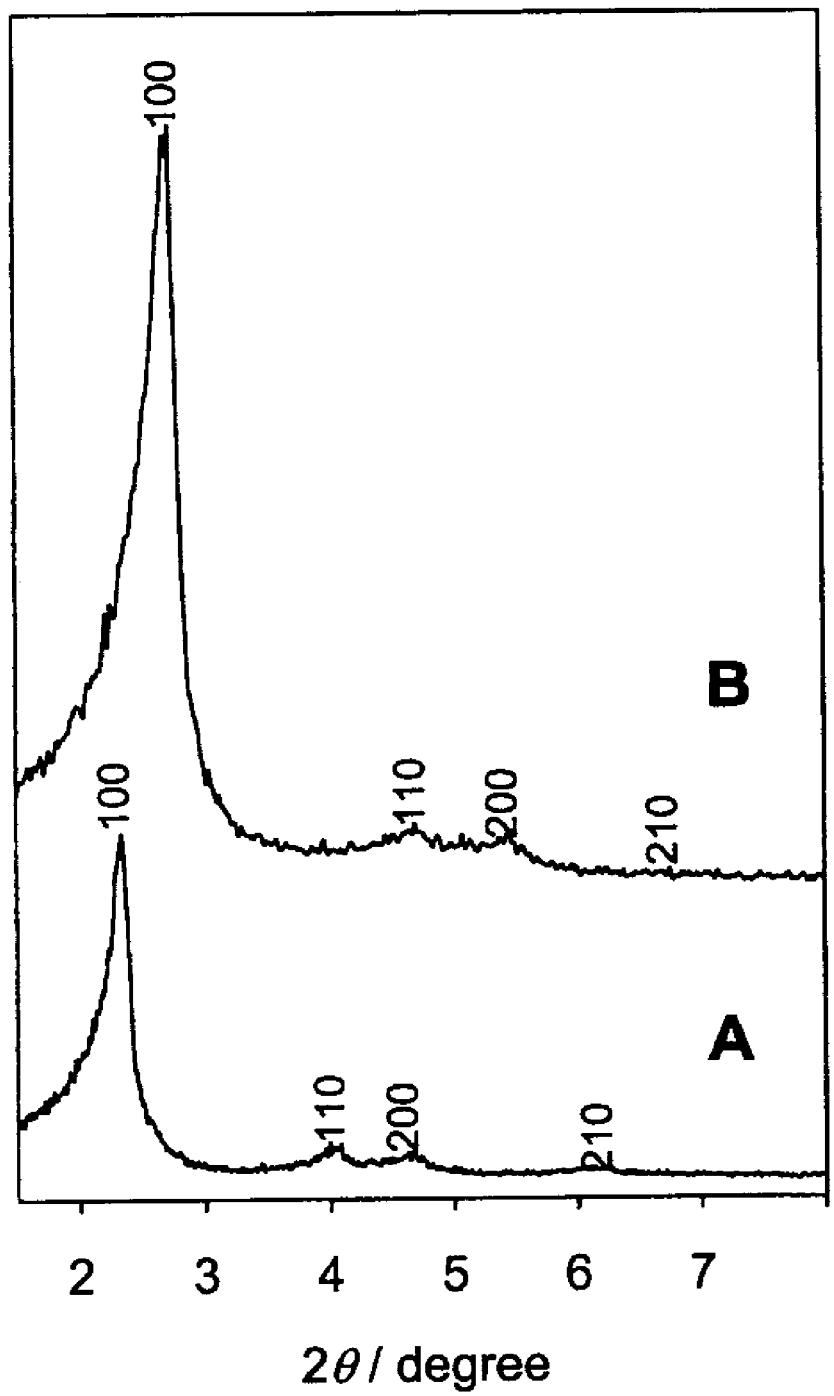
FIG. 1 is X-ray diffraction graphs for the mesoporous material prepared in Example 4.

Hereinafter, the present invention will be explained in more detail with reference to the following Examples.

The present invention provides a gemini surfactant containing siloxane moieties as a structure-directing agent for preparing a mesoporous material, represented by the following formula (1):

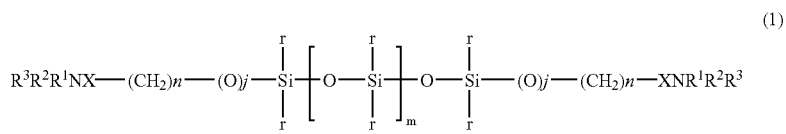

wherein each of $R^1$ and $R^2$ is independently methyl or ethyl group, $R^3$ is an alkyl group having 5 to 40 carbon atoms, X is a halogen atom, each of r is independently a hydrogen atom, methyl group or an alkoxy group having 1 to 10 carbon atoms, j is 0 or 1, m is an integer of from 0 to 10, and n is an integer of from 1 to 12.

The gemini surfactant is prepared by reacting a compound represented by the following formula (2):

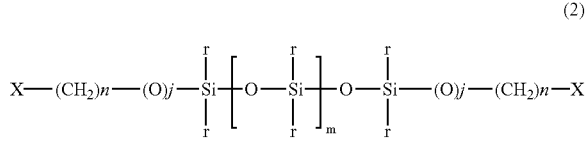

wherein X is a halogen atom, each of r is independently a hydrogen atom, methyl group or an alkyl group having 1 to 10 carbon atoms, j is 0 or 1, m is an integer of from 0 to 10, and n is an integer of from 1 to 12, with a compound represented by the following formula (3):

$$R^3R^2R^1N \quad (3)$$

wherein each of $R^1$ and $R^2$ is independently methyl or ethyl group, and $R^3$ is an alkyl group having 5 to 40 carbon atoms, in a solvent such as ethanol, acetonitrile, toluene or the like as a solvent at 30~120° C., preferably 60~90° C. for 1~100 hours, preferably 24~72 hours.

In the above reaction, the molar ratio of the compound of formula 2 to the compound of formula 3 is 1:2~1:3.

The present invention also provides a method for preparing a mesoporous material in which the gemini surfactant is used as a structure-directing agent.

The method for preparing a mesoporous material preferably comprises the steps of:

(A) mixing an aqueous solution of the gemini surfactant represented by formula 1 with a precursor;

(B) adjusting pH of the mixture of step (A) using an acid or base;

(C) hydrothermally reacting the mixture of step (B);

(D) filtering, washing and drying the material obtained from step (C); and (E) calcining the material obtained from the step (D).

The respective steps will be explained in more detail below.

In step (A), the aqueous solution of the gemini surfactant may be basic or acidic. The basic aqueous solution of the gemini surfactant contains 0.1~5.0% by weight, preferably 0.5~3.0% by weight of the gemini surfactant and a strong base, for example, 0.5~2.0% by weight, preferably 0.7~1.0% by weight of sodium hydroxide. The acidic aqueous solution of the gemini surfactant contains 0.1~5.0% by weight, preferably 0.5~3.0% by weight of the gemini surfactant and a strong acid, for examples, 0.5~10% by weight, preferably of 1.0~5.0% by weight of hydrochloric acid or sulfuric acid.

In step (A), the precursor may be one or more compounds selected from the group consisting of compounds represented by the following formulas (4) to (6):

$$R^4_j R^5_k MY_{4-j-k} \quad (4);$$

$$R^4_h R^5_p Y_{3-h-p} M\text{-}Q\text{-}MY_{3-h-p} R^4_h R^5_p \quad (5); \text{ and}$$

$$M'(Y)_3 \quad (6),$$

wherein each of $R^4$ and $R^5$ is independently an alkyl group having 1 to 10 carbon atoms, Y is an alkoxy group having 1 to 5 carbon atoms, M is Si or Ti atom, M' is Al atom, Q is an alkylene group having 1 to 15 carbon atoms, or an arylene, an alkylarylene or an arylalkylene group, having 6 to 40 carbon atoms, each of j and k is independently an integer of from 0 to 3 provided that 0<j+k<3, and each of h and p is independently an integer of from 0 to 2 provided that 0<h+p<2.

Preferred examples of the precursor include tetraethylorthosilicate (TEOS), tetramethylorthosilicate (TMOS), methyltrimethoxysilane, dimethyldimethoxysilane, trimethylmethoxysilane, methyltriethoxysilane, dimethyldiethoxysilane, trimethylethoxysilane, methyltrichlorosilane, dimethyldichlorosilane, trimethylchlorosilane, bis(trichlorosilyl)methane, 1,2-bis(trichlorosilyl)ethane, bis(trimethoxysilyl)methane, 1,2-bis(triethoxysilyl)ethane, 1,4-bis(trimethoxysilyl)benzene, 1,4-bis(trimethoxysilylethyl)benzene, etc. Tetraethylorthosilicate (TEOS) and tetramethylorthosilicate (TMOS) are preferred.

It is preferred that the precursor is slowly added to the aqueous solution of the surfactant at room temperature under vigorous stirring using an agitator. The amount of the precursor is within the range of 1 to 100 moles, preferably 10 to 50 moles, based on 1 mole of the gemini surfactant. After the precursor is added to the aqueous solution of the surfactant, the reaction mixture is preferably at room temperature for 1 to 2 hours.

In step (B), the pH of the mixture obtained from step (A) is adjusted to 9 to 13, preferably 11 to 12 using an acid or base.

In step (C), the mixture obtained from step (B) is hydrothermally reacted to prepare a mesoporous material. At this step, the temperature and the time of hydrothermal reaction are each within the range of 60~150° C. and 1~144 hours, preferably 12~48 hours.

In step (D), the reaction product obtained from step (C) is filtered, washed 2 to 5 times using distilled water and dried at 50~200° C. for 3~30 hours.

In step (E), the dried reaction product obtained from step (D) is calcined in air or nitrogen atmosphere to remove unreacted surfactant. The calcination is carried out at 400~600° C. for 0.3~30 hours.

The mesoporous material thus prepared is in the form of powders having a pore size of 10 nm or less with uniform pore size distribution.

In addition to the method of the present invention, well-known methods can be used to prepare the mesoporous material, so far as they do not detract from the object of the present invention. For example, a gemini surfactant is dissolved in a solvent, for example, selected from the group consisting of aromatic hydrocarbons such as anisole, xylene, etc.; ketones such as methyl isobutyl ketone, acetone, etc.; ethers such as tetrahydrofuran, isopropyl ether, etc.; alcohols such as ethanol, isopropylalcohol, butanol, etc.; and mixtures thereof, and then an aqueous solution of a precursor is added thereto. Thereafter, the mixture is coated, dried and calcined to prepare a thin mesoporous film.

The present invention will be described in more detail with reference to the following Examples. However, these examples are given for the purpose of illustration and are not to be construed as limiting the scope of the invention.

EXAMPLE 1

Synthesis of Surfactant (1)

$(C_nH_{2n+1}N(CH_3)_2CH_2Si(CH_3)_2OSi(CH_3)_2CH_2N(CH_3)_2 C_nH_{2n+1}Cl_2$ (n=6, 8, 10, 12, 14, 16, 18, 22))

10.0 g of bis(chloromethyl)tetramethyldisiloxane (A) was dissolved in 100 ml of acetonitrile, and 21.4 g of tetradecyldimethylamine (n=14, B) was added thereto. At this time, the molar ratio of A to B was 1:2.05. The solution was refluxed at 82° C. for 24 hours, and then the solvent, acetonitrile was removed in a rotary evaporator to obtain a solid product. The solid product was added to 2 ml of chloroform and dissolved. 500 ml of ethyl acetate was added to the resulting solution, which was then allowed to stand at 0° C. for 12 hours. The recrystallized were filtered, and washed three times with ethyl acetate. The recrystallization, filtration and washing steps were repeated twice more. The resulting material was dried in a vacuum oven at 50° C. for 12 hours to obtain the titled compound in a yield of 42%. Other gemini surfactants (n=6, 8, 10, 12, 16, 18, 22) were prepared in the same manner using alkyldimethylamine compounds having different alkyl chain length ($C_nH_{2n+1}N(CH_3)_2$, n=6, 8, 10, 12, 16, 18, 22) instead of tetradecyldiamine (n=14).

EXAMPLE 2

Synthesis of Surfactant (2)

$(C_nH_{2n+1}N(CH_3)_2CH_2CH_2CH_2OSi(CH_3)_2OSi(CH_3)_2OSi(CH_3)_2OCH_2CH_2CH_2N(CH_3)_2C_nH_{2n+1}Br_2$ (n=6, 8, 10, 12, 16, 18, 22))

7.24 g of BrCH$_2$CH$_2$CH$_2$OSi(CH$_3$)$_2$OSi(CH$_3$)$_2$OSi(CH$_3$)$_2$OCH$_2$CH$_2$CH$_2$Br (A) was dissolved in 200 ml of ethanol, and 9.15 g of octadecyldimethlyamine (n=18, B) was added thereto. At this time, the molar ratio of A to B was 1:2.05. The solution was refluxed for 48 hours, and then the solvent, ethanol was removed in a rotary evaporator to obtain a solid product. The solid product was added to 2 ml of chloroform and dissolved. 500 ml of ethyl acetate was added to the resulting solution, which was then allowed to stand at 0° C. for 12 hours. The recrystallized were filtered, and washed three times with ethyl acetate. The recrystallization, filtration and washing steps were repeated twice more. The resulting material was dried in a vacuum oven at 50° C. for 12 hours to obtain the titled compound in a yield of 40%. Other gemini surfactants (n=6, 8, 10, 12, 16, 22) were prepared in the same manner using alkyldimethylamine compounds having different alkyl chain length (C$_n$H$_{2n+1}$N(CH$_3$)$_2$, n=6, 8, 10, 12, 16, 22) instead of octadecyldimethlyamine (n=18).

EXAMPLE 3

Synthesis of Surfactant (3)

(C$_n$H$_{2n+1}$N(CH$_3$)$_2$CH$_2$CH$_2$OSi(CH$_3$)$_2$OSi(CH$_3$)$_2$OSi(CH$_3$)$_2$OCH$_2$CH$_2$N(CH$_3$)$_2$C$_n$H$_{2n+1}$Br$_2$, n=6, 8, 10, 12, 16, 18, 22)

7.01 g of BrCH$_2$CH$_2$OSi(CH$_3$)$_2$OSi(CH$_3$)$_2$OSi(CH$_3$)$_2$OCH$_2$CH$_2$Br (A) was dissolved in 200 ml of ethanol, and 9.15 g of octadecyldimethylamine (n=18, B) was added thereto. At this time, the molar ratio of A to B was 1:2.05. The solution was refluxed for 48 hours, and then the solvent, ethanol was removed in a rotary evaporator to obtain a solid product. The solid product was added to 2 ml of chloroform and dissolved. 500 ml of ethyl acetate was added to the resulting solution, which was then allowed to stand at 0° C. for 12 hours. The recrystallized were filtered, and washed three times with ethyl acetate. The recrystallization, filtration and washing steps were repeated twice more. The resulting material was dried in a vacuum oven at 50° C. for 12 hours to obtain the titled compound in a yield of 35%. Other gemini surfactants (n=6, 8, 10, 12, 16, 22) were prepared in the same manner using alkyldimethylamine compounds having different alkyl chain length (C$_n$H$_{2n+1}$N(CH$_3$)$_2$, n=6, 8, 10, 12, 16, 22) instead of octadecyldimethlyamine (n=18).

EXAMPLE 4

Preparation of Powdered Mesoporous Material (1)

0.84 g of C$_{14}$H$_{29}$N(CH$_3$)$_2$CH$_2$Si(CH$_3$)$_2$OSi(CH$_3$)$_2$CH$_2$N(CH$_3$)$_2$C$_{14}$H$_{29}$Cl$_2$ (n=14), one of the gemini surfactants synthesized in Example 1 and 1.21 g of sodium hydroxide were dissolved in 158 g of distilled water to obtain an aqueous solution. While the aqueous solution was vigorously stirred using a magnetic stirrer, 12.0 g of TEOS was added. At this time, the molar ratio of the reactants in the mixture was 0.04:1:0.5:150 (surfactant:TEOS:NaOH:H$_2$O). pH of the resultant solution was in the range of pH 9~13 and thus pH regulation was not specially done. The reactant mixture was stirred at room temperature for 1 hour, and reacted in an oven at 100° C. for 24 hours. Then, the resulting precipitates were filtered, washed with distilled water, and dried at 100° C. The dried precipitates were calcined in air at 550° C. for 10 hours to remove the surfactant contained therein. FIG. 1 is X-ray diffraction graphs for the mesoporous material thus prepared. In FIG. 1, graph A was obtained from the material before calcination, and graph B was obtained from the material after calcination. From FIG. 1, about 10% of structural shrinkage is observed after calcination. However, the X-ray diffraction patterns give (100), (110) and (200) peaks, which represents a second-dimensional hexagonal arrangement at low angle regions, regardless of calcination. Accordingly, FIG. 1 shows that the mesoporous silica material prepared according to the present invention has excellent structural uniformity.

Figure 2:
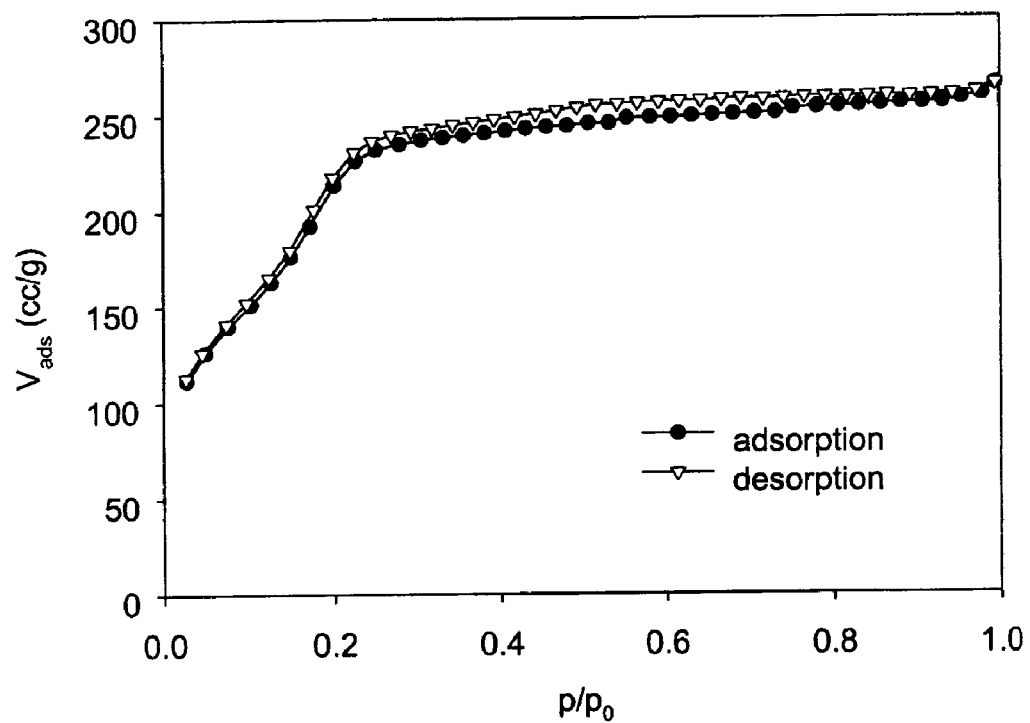
FIG. 2 is an adsorption-desorption isotherm for the mesoporous material prepared in Example 4 at liquid nitrogen temperature.
Figure 3:
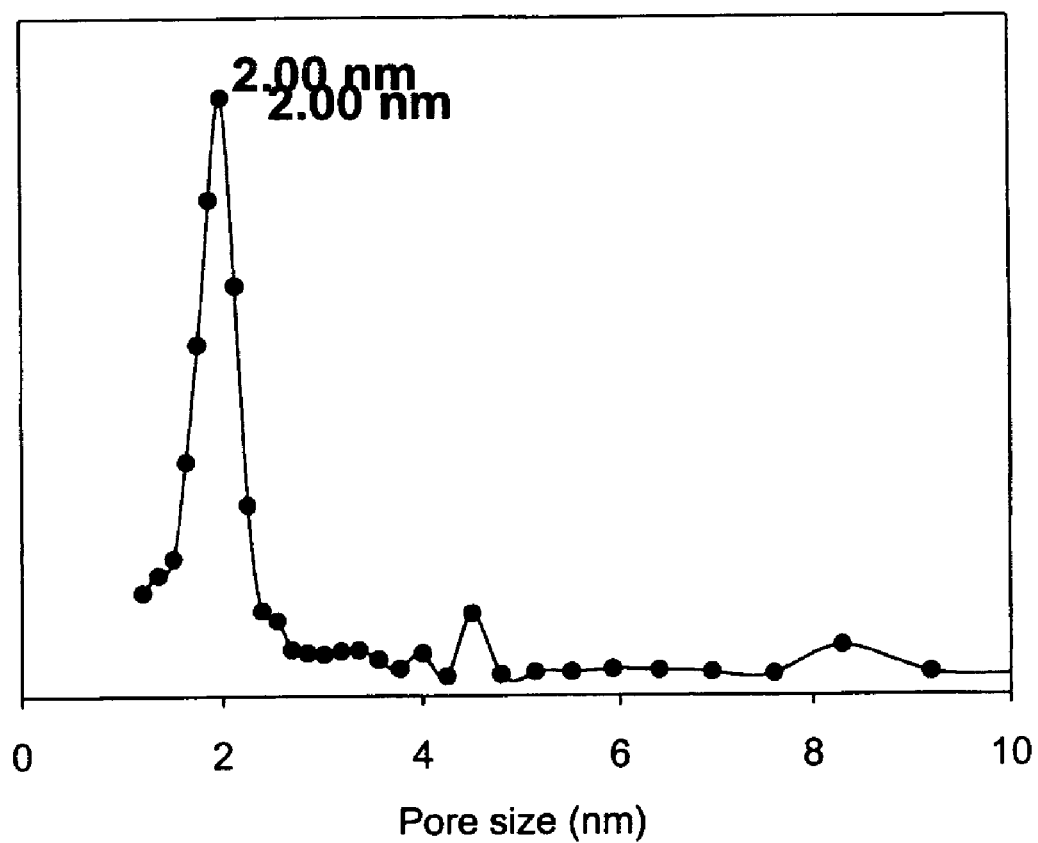
FIG. 3 is a pore size distribution graph obtained from the adsorption-desorption isotherm of FIG. 2 by the BJH (Barrett-Joyner-Halenda) method.

FIG. 2 is an adsorption-desorption isotherm for the calcined product. BET surface area obtained from the adsorption-desorption isotherm of FIG. 2 was 840 m$^2$/g per 1 g. The adsorption-desorption isotherm of nitrogen in FIG. 2 represents a feature of mesoporous materials according to IUPAC definition. In FIG. 2, adsorption amount of nitrogen was suddenly increased around 0.2 of p/po value. FIG. 3 is a pore size distribution graph obtained from the adsorption-desorption isotherm of FIG. 2 by the BJH (Barrett-Joyner-Halenda) method. In FIG. 3, the peak has a shape wherein the pore size is crowded around 2.00 nm (line width at middle height is 0.5 nm or less).

Figure 4:
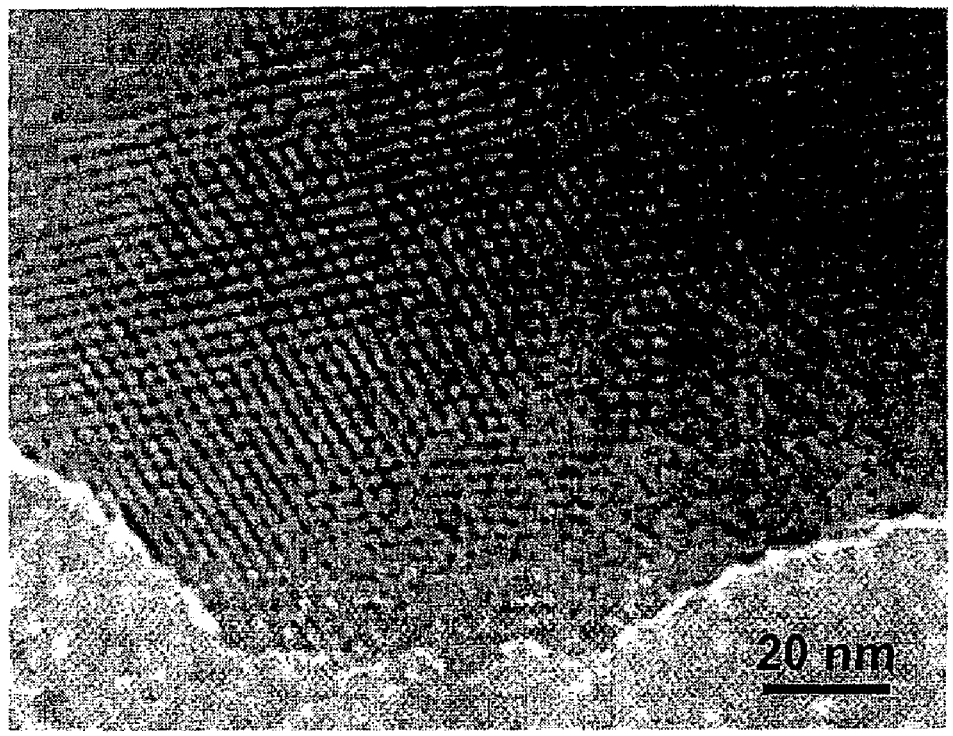
FIG. 4 is an image of Transmission Electron Microscopy for the mesoporous material prepared in Example 4.

FIG. 4 is an image of Transmission Electron Microscopy for the resulting mesoporous material. From the image, it is known that the prepared material is mesoporous material having uniform pore distribution.

EXAMPLE 5

Preparation of Powdered Mesoporous Material (2)

0.91 g of C$_{14}$H$_{29}$N(CH$_3$)$_2$CH$_2$Si(CH$_3$)$_2$OSi(CH$_3$)$_2$CH$_2$N(CH$_3$)$_2$C$_{14}$H$_{29}$Cl$_2$ (n=14), one of the gemini surfactants synthesized in Example 1 and 2.02 g of sodium hydroxide were dissolved in 264 g of distilled water to obtain an aqueous solution. While the aqueous solution was vigorously stirred using a magnetic stirrer, 20.0 g of TEOS was added. At this time, the molar ratio of the reactants in the mixture was 0.12:1:0.5:150 (surfactant:TEOS:NaOH:H$_2$O). pH of the resultant solution was in the range of pH 9~13 and thus pH regulation was not specially done. The reactant mixture was stirred at room temperature for 1 hour, and reacted in an oven at 100° C. for 24 hours. Then, the resulting precipitates were filtered, washed with distilled water, and dried at 100° C. The dried precipitates were calcined in air at 550° C. for 10 hours to remove the surfactant contained therein.

On the other hand, 1.0 g of the material obtained right after hydrothermal reaction was washed two times using a mixture 10 g of ethanol and 5 g of 35% HCl solution to remove surfactant and cancined in air at 550° C. for 10 hours for comparison.

Figure 5:
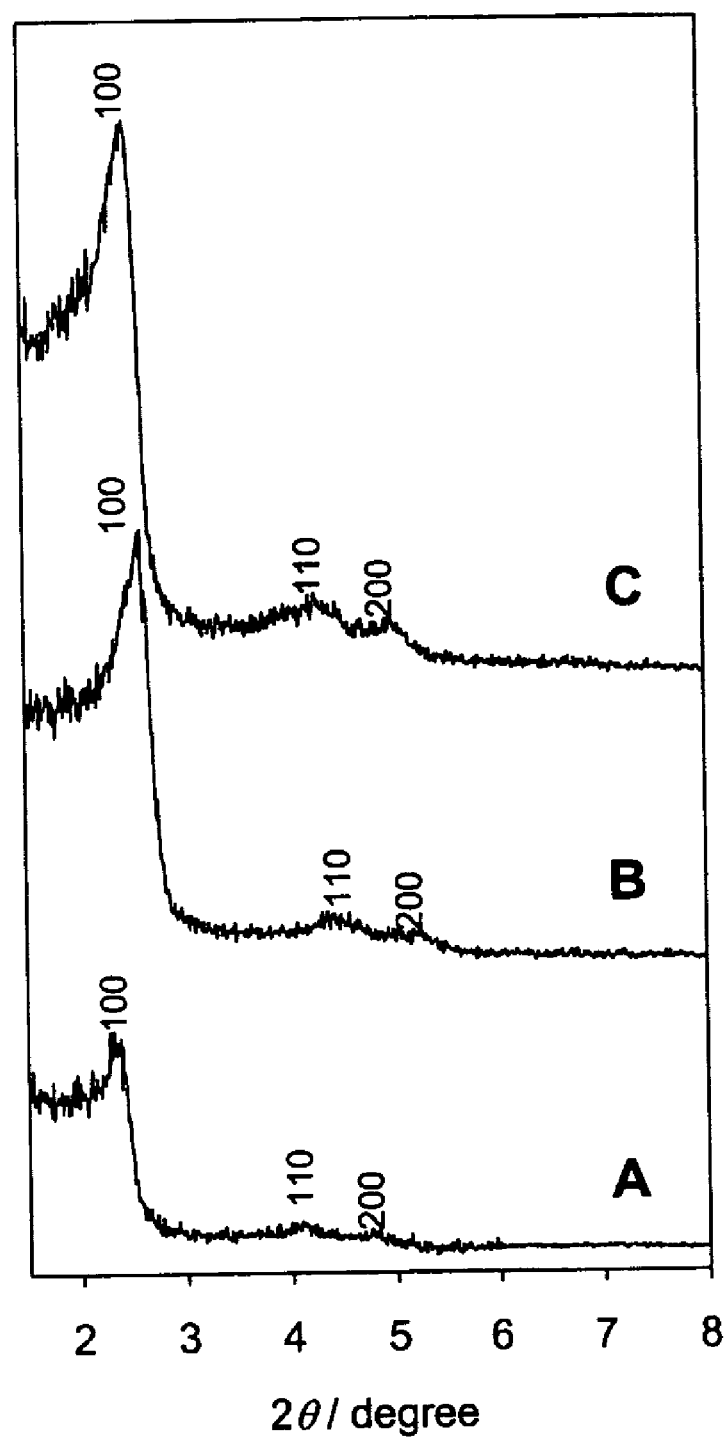
FIG. 5 is X-ray diffraction graphs for the mesoporous materials prepared in Example 5.

FIG. 5 is X-ray diffraction graphs for the mesoporous materials thus prepared. In FIG. 5, graph A was obtained from the material before calcination, graph B was obtained from the material wherein the surfactant had been removed by calcination, graph C was obtained from the material which had been calcined after the surfactant had been removed by solvent extraction. The lattice constants obtained from graph B and C were respectively 4.04 nm and 4.09 nm, which were very similar to each other.

Figure 6:
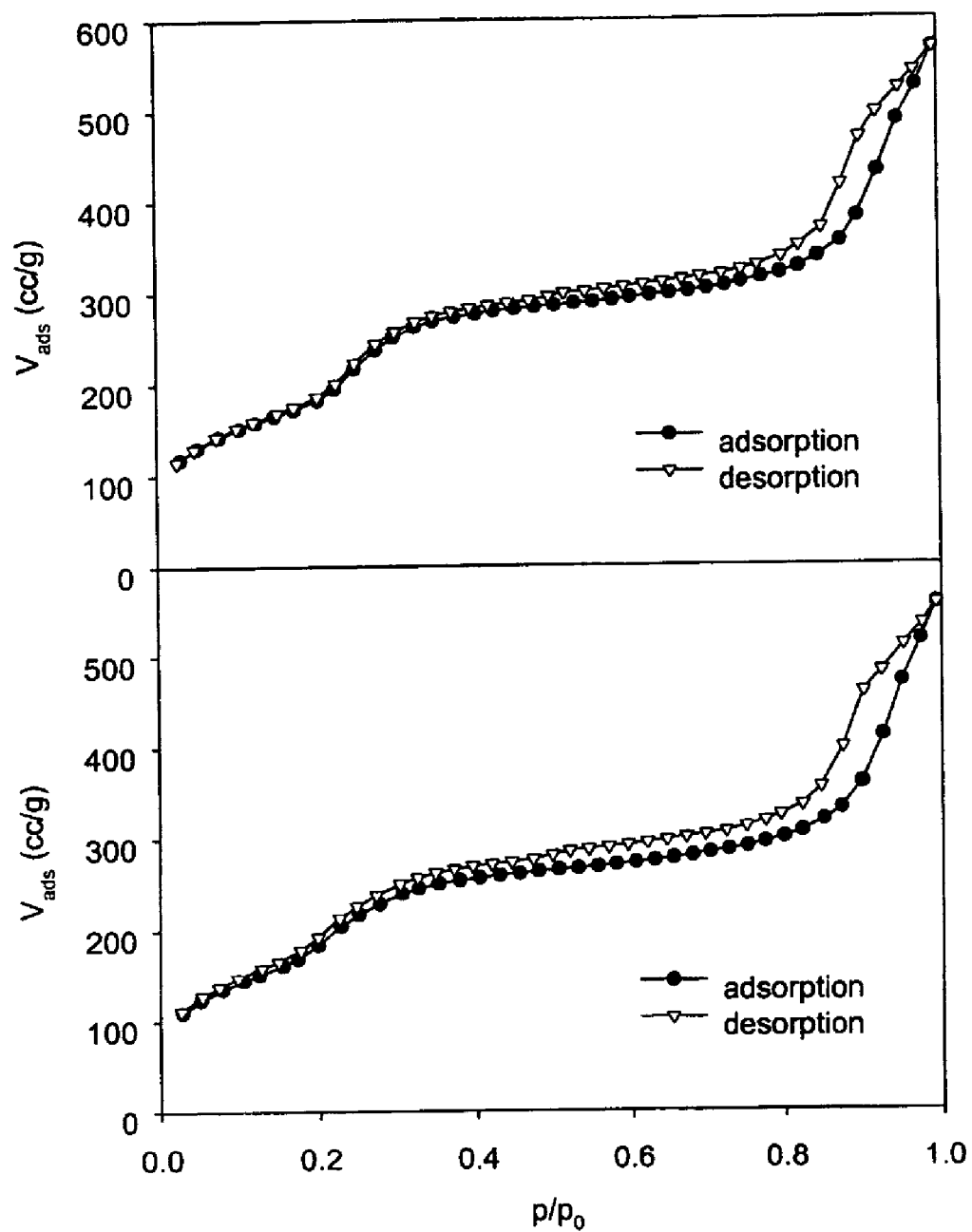
FIG. 6 is adsorption-desorption isotherms for the mesoporous materials prepared in Example 5 at liquid nitrogen temperature.
Figure 7:
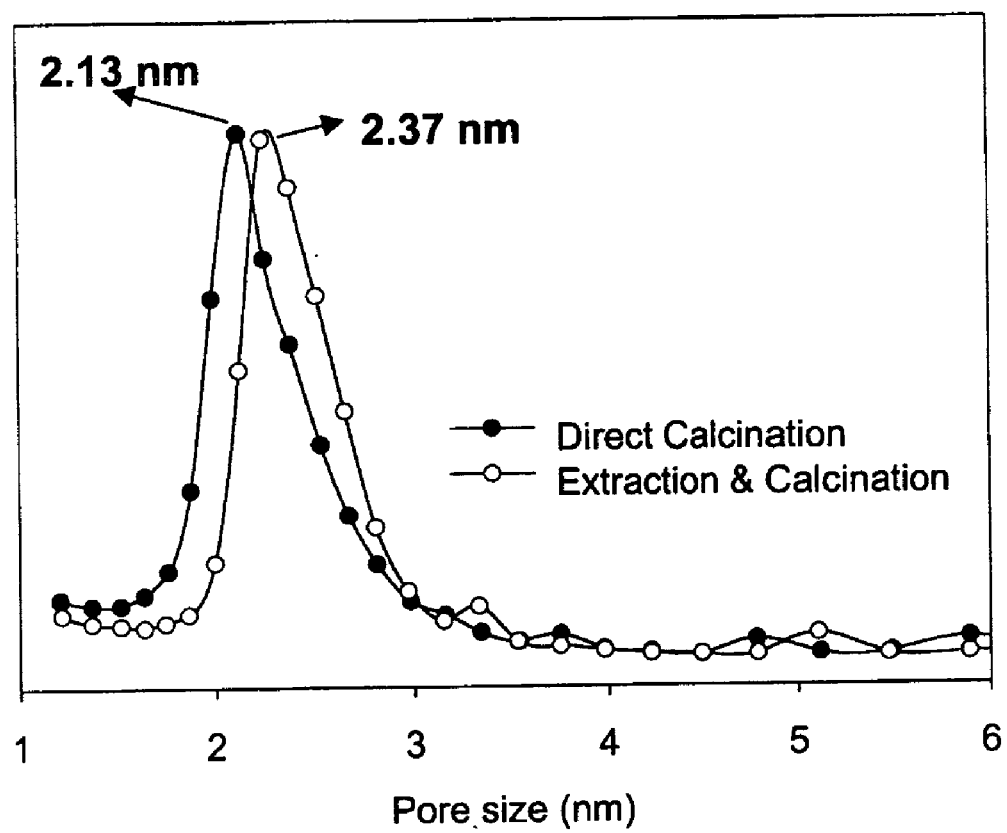
FIG. 7 is pore size distribution graphs obtained from the adsorption-desorption isotherms of FIG. 6 by the BJH method.

FIG. 6 is adsorption-desorption isotherms for the products which is calcined with and without solvent extraction of the surfactant. From FIG. 6, BET surface area and pore size was calculated. The calcined material wherein the surfactant had been removed before calcinations had BET surface area of 827 $m^2$ per 1 g and pore size of 2.13 nm. The calcined material wherein the surfactant was removed by solvent extraction had BET surface area of 853 $m^2$ per 1 g and pore size of 2.37 nm. FIG. 7 is pore size distribution graphs obtained from the adsorption-desorption isotherms of FIG. 6 by the BJH method. From FIG. 7, it is known that pore size was varied from 2.13 nm to 2.37 nm when the surfactant was removed before calcination. In this regard, the difference of lattice constant and a pore size represents wall thickness of mesoporous material. In the above two case, wall thickness was respectively 1.91 nm and 1.72 nm. Accordingly, it is known that there happened a difference of wall thickness according to the method of removing the surfactant. This is because siloxane moiety was deposited through calcination when the calcination was processed without removing the surfactant. So, the wall thickness of the mesoporous material which was produced without solvent extraction of the surfactant is thicker than that of the mesoporous material which was produced through solvent extraction of the surfactant and calcination. This can be a merit of the present invention.

EXAMPLE 6

Preparation of Powdered Mesoporous Material (3)

Mesoporous materials were prepared respectively using each of three gemini surfactants having different alkyl chain length, synthesized in Example 1. Each of gemini surfactants with an alkyl chain length of 12, 14 and 16 was respectively dissolved in 158 g of distilled water in each amount of 0.78 g, 0.84 g and 0.90 g, and then 1.21 g of sodium hydroxide was added thereto to obtain an aqueous solution. While the aqueous solution was vigorously stirred using a magnetic stirrer, 12.0 g of TEOS was added. The reaction mixture was stirred at room temperature for 1 hour, and reacted in an oven at 100° C. for 24 hours. The resulting precipitates were filtered, washed with distilled water, and dried at 100° C.

Figure 8:
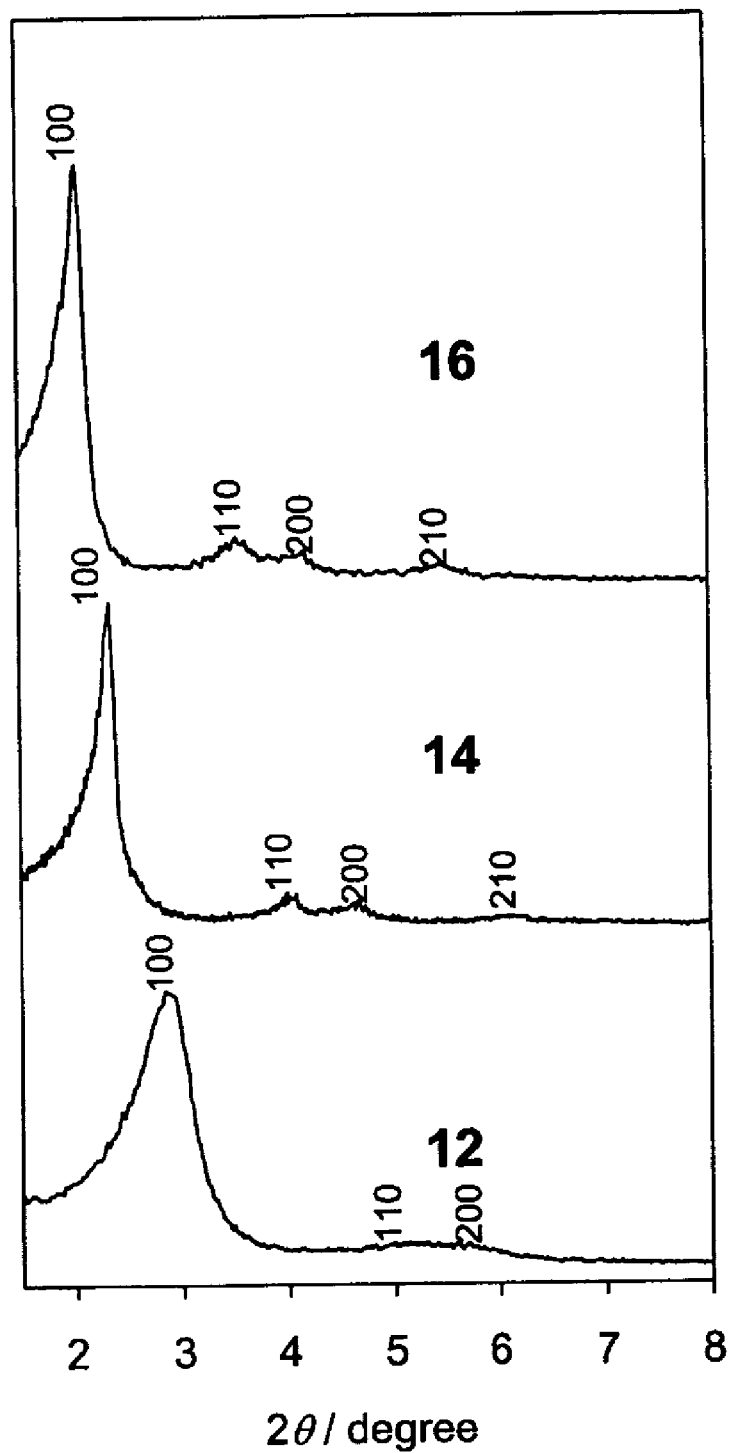
FIG. 8 is X-ray diffraction graphs for the mesoporous materials prepared in Example 6.
Figure 9:
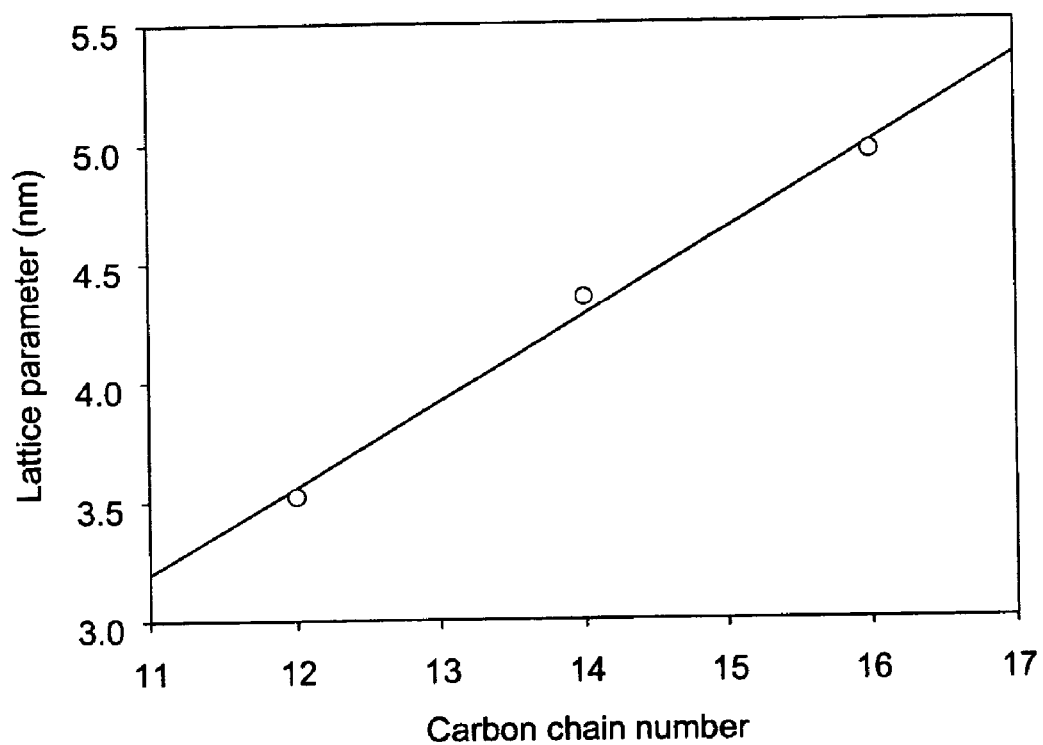
FIG. 9 is a graph showing values of lattice constant a for the mesoporous material, which is calculated from the X-ray diffraction graph of FIG. 8, and plotted versus carbon number n of alkyl chain.

FIG. 8 is X-ray diffraction graphs for the mesoporous materials thus prepared. The X-ray diffraction patterns give (100), (110) and (200) peaks, which represents a second-dimensional hexagonal arrangement, at low angle regions. Accordingly, FIG. 8 shows that the mesoporous silca materials have excellent structural uniformity. The X-ray diffraction patterns give lattice constants of 3.52 nm, 4.35 nm and 4.96 nm, which is proportional to the number of the carbon atoms of alkyl chains. FIG. 9 is a graph showing values of lattice constant a for the mesoporous material, which is calculated from the X-ray diffraction graph of FIG. 8, and plotted versus carbon number n of alkyl chain. From FIG. 9, it is known that the lattice constant increases linearly from 3.5 nm to 5.0 nm according to the length of alkyl chain in the surfactants. This means that pore size of the silica material can be regulated by changing the structure of the surfactant according to the present invention. Accordingly, it is verified that the gemini surfactants according to present invention is a new and excellent structure-directing agent which can regulate the pore size of the mesoporous material and improve the structure uniformity of the mesorporous material.

EXAMPLE 7

Preparation of Powdered Mesoporous Material (4)

Figure 10:
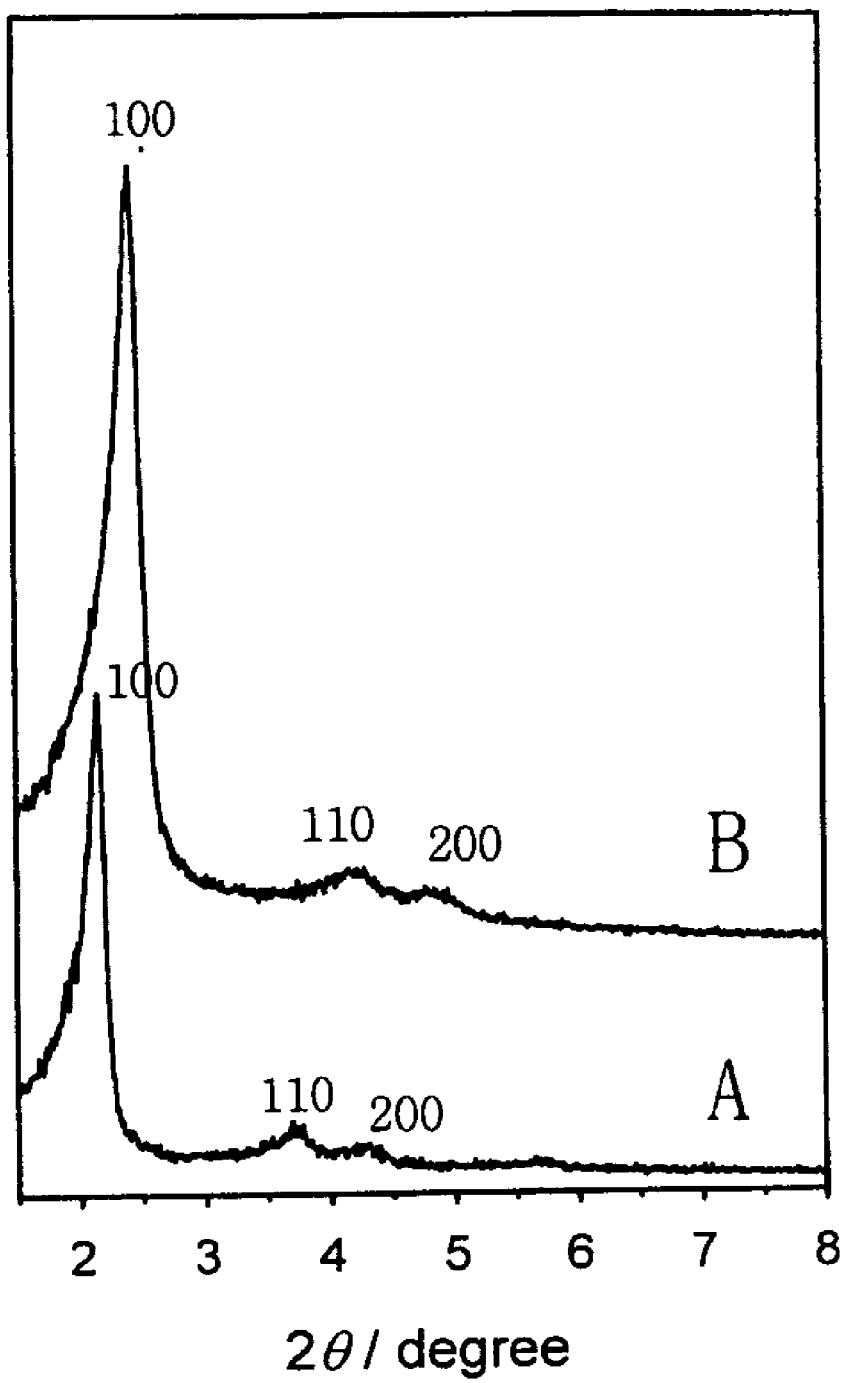
FIG. 10 is X-ray diffraction graphs for the mesoporous material prepared in Example 7.

0.42 g of $C_{18}H_{37}N(CH_3)_2CH_2CH_2CH_2OSi(CH_3)_2OSi(CH_3)_2OSi(CH_3)_2OCH_2CH_2CH_2N(CH_3)_2C_{18}H_{37}Br_2$ (n=18), one of the gemini surfactants synthesized in Example 2 and 0.202 g of sodium hydroxide were dissolved in 26.5 g of distilled water to obtain an aqueous solution. While the aqueous solution was vigorously stirred using a magnetic stirrer, 2.0 g of TEOS was added. At this time, the molar ratio of the reactants in the mixture was 0.04:1:0.5:150 (surfactant: TEOS:NaOH:$H_2O$). The reactant mixture was stirred at room temperature for 1 hour, and reacted in an oven at 100° C. for 24 hours. Then, the resulting precipitates were filtered, washed with distilled water, and dried at 100° C. The dried precipitates were calcined in air at 550° C. for 10 hours to remove the surfactant contained therein. FIG. 10 is X-ray diffraction graphs for the mesoporous material thus prepared. In FIG. 10, graph A was obtained from the material before calcination, and graph B was obtained from the material after calcination. From FIG. 10, about 10% of structural shrinkage was observed after calcination. However, the X-ray diffraction patterns give (100), (110) and (200) peaks, which represents a second-dimensional hexagonal arrangement in low angle regions, after calcination. Accordingly, FIG. 10 shows that the mesoporous silica material has excellent structural uniformity.

Figure 11:
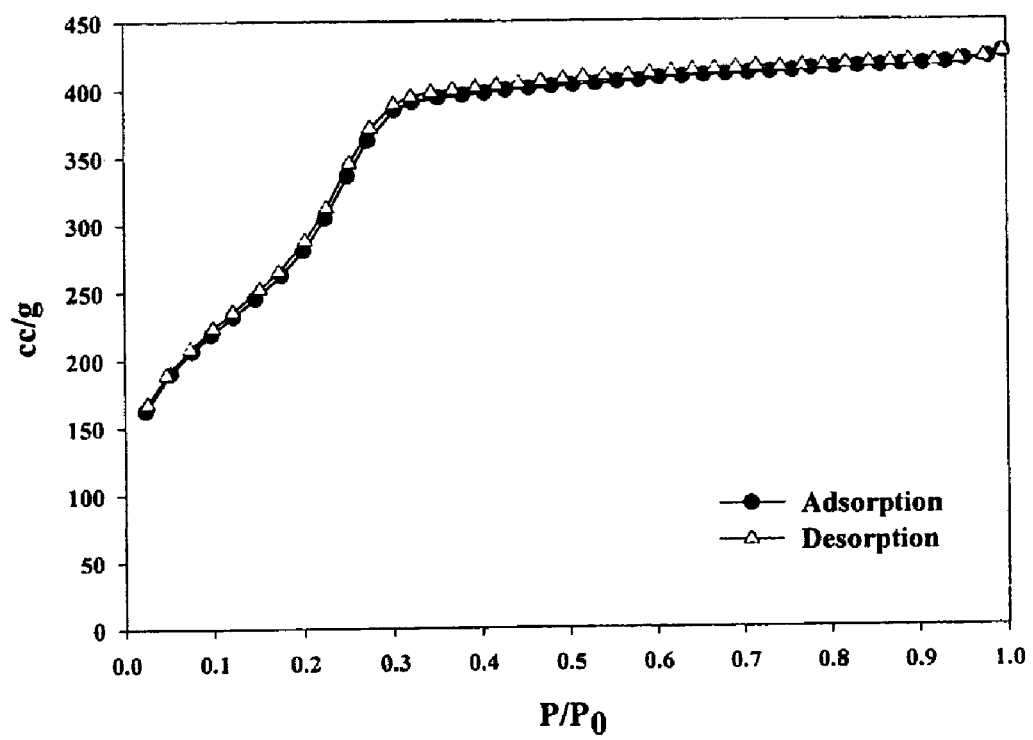
FIG. 11 is an adsorption-desorption isotherm for the mesoporous material prepared in Example 7 at liquid nitrogen temperature.
Figure 12:
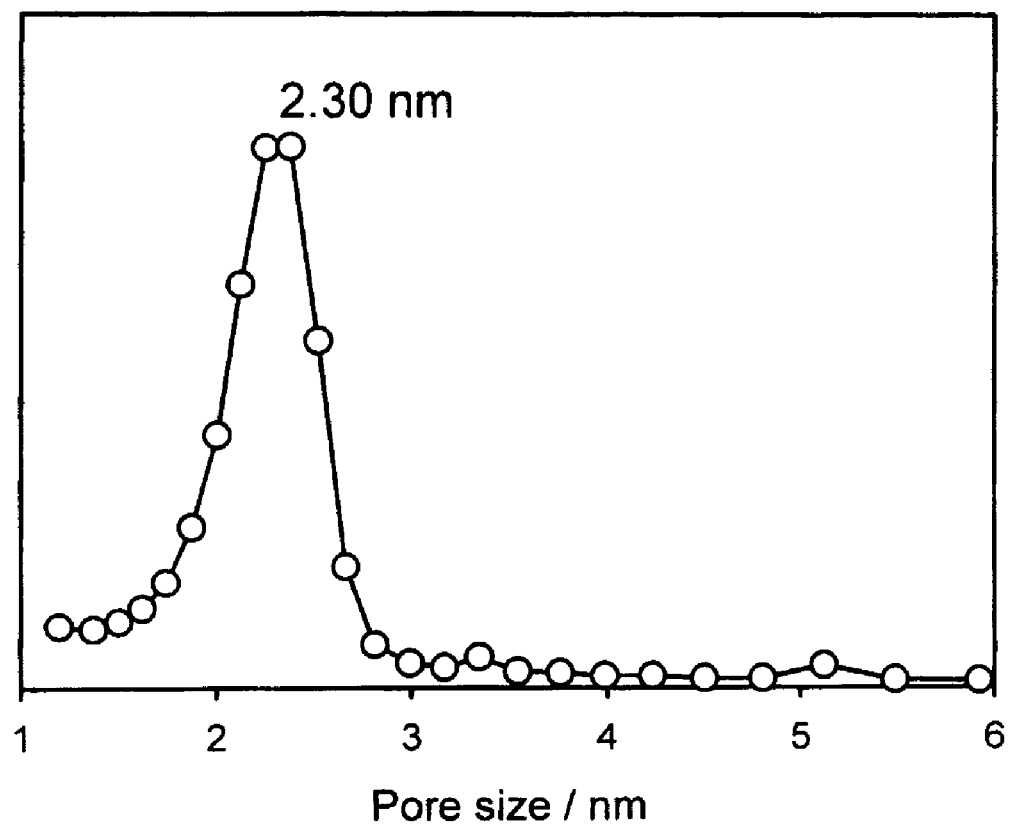
FIG. 12 is a pore size distribution graph obtained from the adsorption-desorption isotherm of FIG. 11 by the BJH method.

FIG. 11 is an adsorption-desorption isotherm for the calcined product, and FIG. 12 is a pore size distribution graph obtained from the adsorption-desorption isotherm of FIG. 11 by the BJH method. BET surface area obtained from the adsorption-desorption isotherm of FIG. 11 was 1336 $m^2/g$ per 1 g. The pore size was 2.30 nm, as shown in FIG. 12.

EXAMPLE 8

Preparation of Powdered Mesoporous Material (5)

Figure 13:
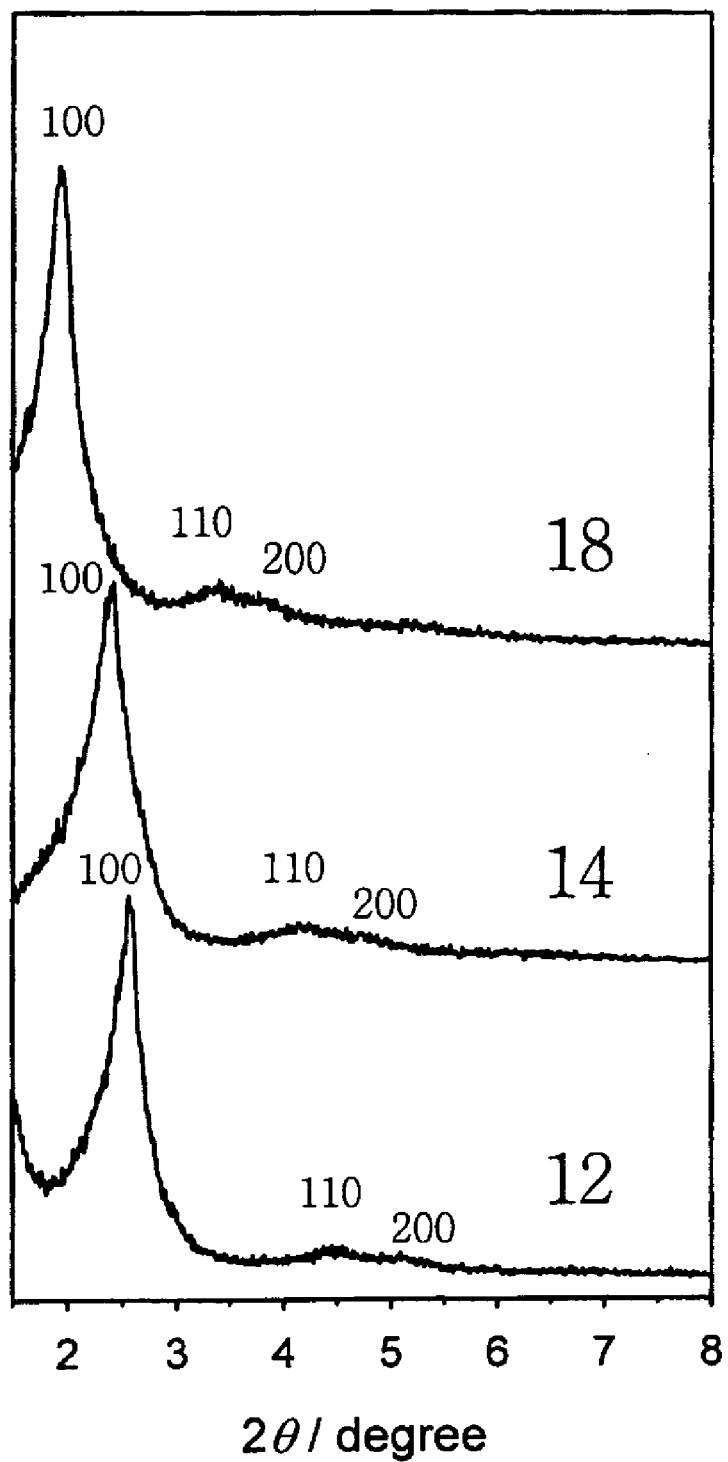
FIG. 13 is X-ray diffraction graphs for the mesoporous materials prepared in Example 8.
Figure 14:
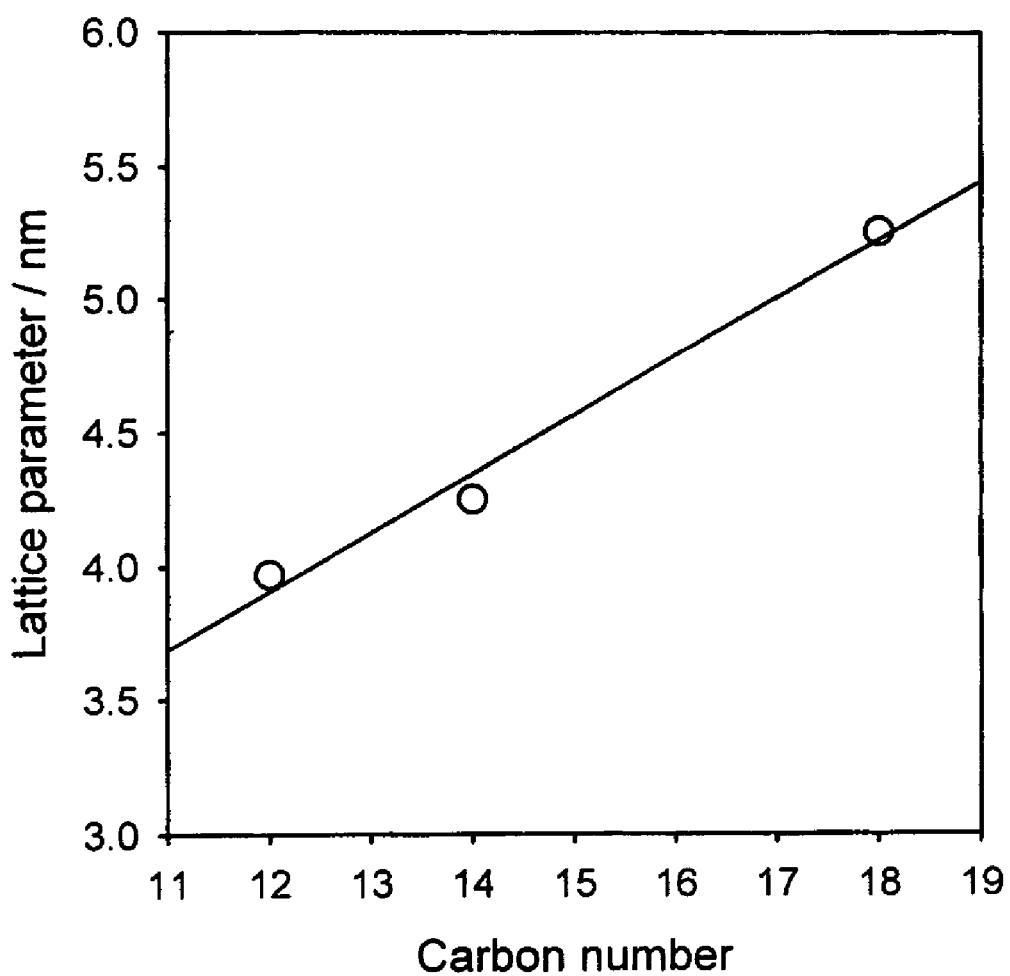
FIG. 14 is a graph showing values of lattice constant a for the mesoporous material, which is calculated from the X-ray diffraction graph of FIG. 13, and plotted versus carbon number n of alkyl chain.

Mesoporous materials were prepared respectively using each of three gemini surfactants having different alkyl chain lengths synthesized in Example 3. Each of gemini surfactants with an alkyl chain length of 12, 14 and 18 was respectively dissolved in 66.1 g of distilled water in each amount of 0.86 g, 0.92 g and 1.03 g, and then 0.51 g of sodium hydroxide was added thereto to obtain an aqueous solution. While the aqueous solution was vigorously stirred using a magnetic stirrer, 5.0 g of TEOS was added. At this time, the molar ratio of the reaction reactants in the mixture was 0.04:1:0.5:150 (surfactant: TEOS:NaOH:$H_2O$). The reaction mixture was stirred at room temperature for 1 hour, and reacted in an oven at 100° C. for 24 hours. The resulting precipitates were filtered, washed with distilled water, and dried at 100° C. FIG. 13 is X-ray diffraction graphs for the mesoporous materials thus prepared. The X-ray diffraction patterns give lattice constants of 3.97 nm, 4.25 nm and 5.26 nm. The lattice constants were proportional to the number of the carbon atoms of alkyl chains as seen in FIG. 14.

EXAMPLE 9

Preparation of Powdered Mesoporous Material (6)

Figure 15:
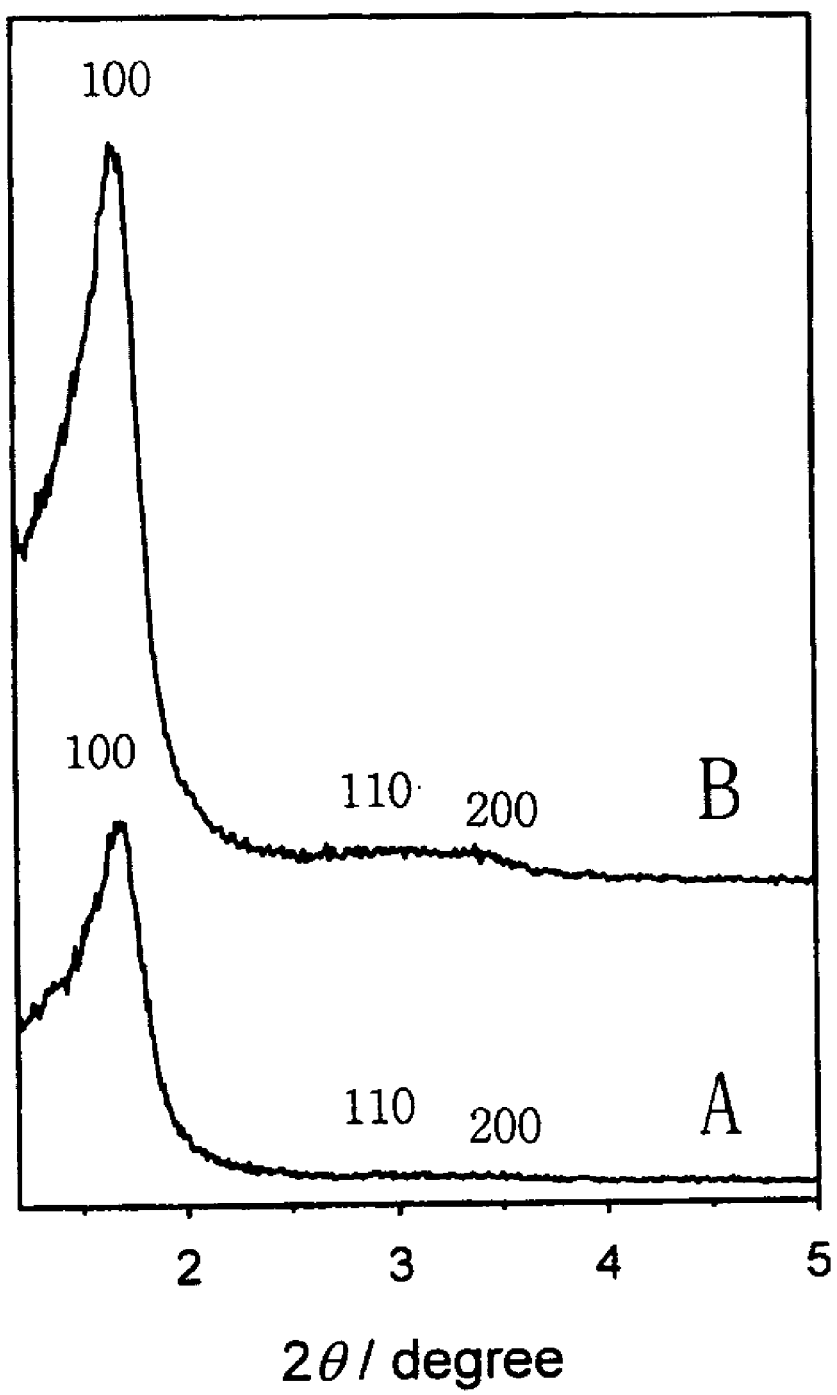
FIG. 15 is X-ray diffraction graphs for the mesoporous material having an organic-inorganic composite skeleton prepared in Example 9.

69 g of $C_{18}H_{37}N(CH_3)_2CH_2CH_2CH_2OSi(CH_3)_2OSi(CH_3)_2OSi(CH_3)_2OCH_2CH_2CH_2N(CH_3)_2C_{18}H_{37}Br_2$ (n=18) synthesized in Example 2 and 0.21 g of sodium hydroxide were dissolved in 12.0 g of distilled water to obtain an aqueous solution. While the aqueous solution was vigorously stirred using a magnetic stirrer, 0.70 g of bis (triethoxysilyl)ethane (BTME) was added. At this time, the molar ratio of the reactants in the mixture was 0.04:1:2.62:356 (surfactant: BTME:NaOH:$H_2O$). The reaction mixture was stirred at room temperature for 20 hours, and reacted in an oven at 100° C. for 20 hours. Then, the resulting precipitates were filtered, washed with distilled water, and dried at 100° C. 1.0 g of the dried precipitates were washed twice with 10 g of ethanol and 5 g of 35% HCl. FIG. 15 is X-ray diffraction graphs for the mesoporous material thus prepared. In FIG. 15, graph A was obtained from the material before calcination, and graph B was obtained from the material after calcination.

EXAMPLE 10

Preparation of Mesoporous Material (7) in the Form of Thin Film

As a solvent for preparing mesoporous thin film, a mixture of 1-propanol and 2-butanol (1:1 weight ratio) was used. Solutions (a) were respectively prepared by dissolving each of the gemini surfactants(n=12, 14, 16, 18) in 6 g of the solvent in the amount of 3 g. Solution (b) was prepared by mixing 6 g of TEOS and 2.2 g of HCl aqueous solution (1M) and refluxing for 1 hour while heating the solution. After solution (b) was cooled to room temperature, it was mixed with each of solutions (a), and stirred for 1 hour. The resulting solutions were respectively sprayed on a silicon wafer in a rotation of 3000 rpm. The coated films were dried for 24 hours at room temperature to obtain mesoporous thin films.

Figure 16:
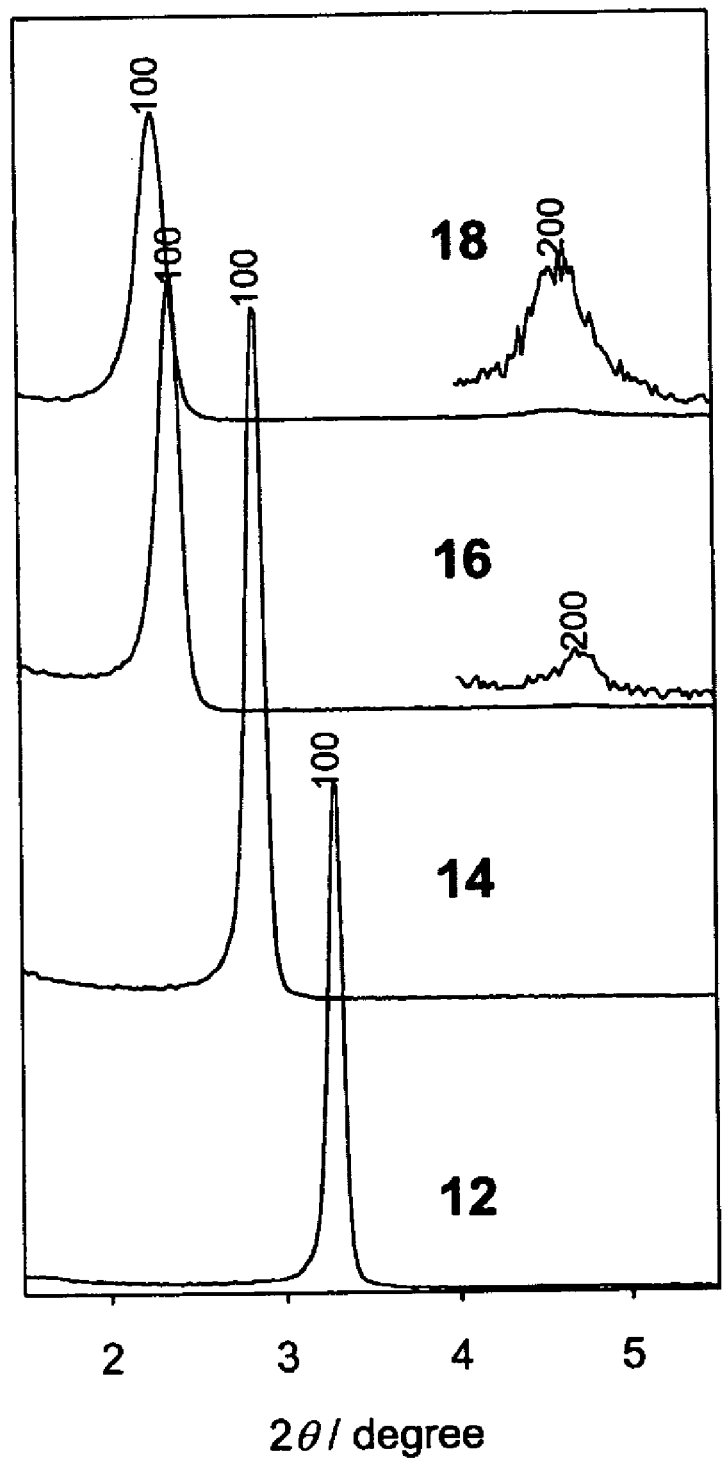
FIG. 16 is X-ray diffraction graphs for the mesoporous materials in the form of thin film prepared in Example 10.

FIG. 16 is X-ray diffraction graphs for the mesoporous materials in the form of thin film prepared in Example 10. FIG. 16 shows that the thin films prepared in Example 10 have a structure on which mesopores were distributed uniformly. Accordingly, the gemini surfactants according to the present invention can be used as a structure-directing agent of a mesoporous material in the form of thin film as well as of powdered mesoporous material.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A gemini surfactant represented by the following formula (1):

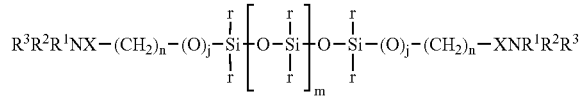

(1)

wherein each of $R^1$ and $R^2$ is independently methyl or ethyl group, $R^3$ is an alkyl group having 5 to 40 carbon atoms, X is a halogen atom, each of r is independently a hydrogen atom, methyl group or an alkoxy group having 1 to 10 carbon atoms, j is 0 or 1, m is an integer of from 0 to 10, and n is an integer of from 1 to 12.

2. A method of preparing the gemini surfactant according to claim 1, the method comprising the steps of:

mixing a compound represented by the following formula (2):

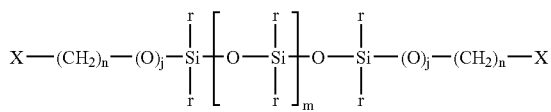

(2)

wherein X is a halogen atom, each of r is independently a hydrogen atom, methyl group or an alkyl group having 1 to 10 carbon atoms, j is 0 or 1, m is an integer of from 0 to 10 and n is an integer of from 1 to 12, and a compound represented by the following formula (3):

$$R^3R^2R^1N \quad (3)$$

wherein each of $R^1$ and $R^2$ is independently methyl or ethyl group, and $R^3$ is an alkyl group having 5 to 40 carbon atoms, in a molar ratio of 1:2~1:3; and reacting the mixture in ethanol, acetonitrile, or toluene as a solvent at 30~120° C. for 1~100 hours.

3. A method for preparing a mesoporous material using the gemini surfactant according to claim 1 as a structure-directing agent.

4. The method according to claim 3, wherein the mesoporous material is prepared through the following steps:

(A) mixing an aqueous solution of the gemini surfactant with a precursor;

(B) adjusting pH of the mixture of step (A) using an acid or base;

(C) hydrothermally reacting the mixture of step (B);

(D) filtering, washing and drying the material obtained from step (C); and (E) calcining the material obtained from the step (D).

5. The method according to claim 4, wherein in step (A) the aqueous solution is a basic solution containing 0.1~5.0% by weight of the gemini surfactant and 0.5~2.0% by weight of a strong base, or an acidic solution containing 0.1~5.0% by eight of the gemini surfactant and 0.5~2.0% by weight of a strong acid.

6. The method according to claim 4, wherein in step (A) the precursor is one or more compounds selected from the group consisting of compounds represented by the following formulas (4) to (6):

(4);

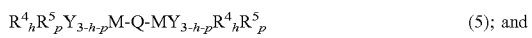

(5); and

(6), wherein each of $R^4$ and $R^5$ is independently an alkyl group having 1 to 10 carbon atoms, Y is an alkoxy group having 1 to 5 carbon atoms, M is Si or Ti atom, M' is Al atom, Q is an alkylene group having 1 to 15 carbon atoms, or an arylene, an alkylarylene or an arylalkylene group, having 6 to 40 carbon atoms, each of j and k is independently an integer of from 0 to 3 provided that $0 \leq j+k \leq 3$, and each of h and p is independently an integer of from 0 to 2 provided that $0<h+p \leq 2$.

7. The method according to claim 6, wherein the precursor is mixed in an amount of 1 to 100 moles per 1 mole of the gemini surfactant.

8. The method according to claim 4, wherein in step (C) the hydrothermal reaction is processed at 60~150° C. for 1 to 144 hours.

9. The method according to claim 4, wherein in step (D) the material obtained form step (C) is filtered, washed 2 to 5 times using distilled water, and dried at 50~200° C. for 3 to 30 hours.

10. The method according to claim 4, wherein in step (E) the material obtained from step (D) is calcined at 400~600° C. under nitrogen atmosphere for 0.5~30 hours.

11. The method according to claim 3, wherein the mesoporous material is prepared in the form of a thin film through the following steps:

dissolving the gemini surfactant in a solvent selected form the group consisting of aromatic hydrocarbons, ketones, ethers, alcohols and mixtures thereof;

mixing a precursor aqueous solution of the Gemini surfactant;

coating the resulting solution to form the thin film; and drying and calcining the thin film.

* * * * *